(12) United States Patent
Cluzeau et al.

(10) Patent No.: US 8,895,520 B2
(45) Date of Patent: Nov. 25, 2014

(54) METHOD FOR TREATING A HUMAN PATENT SUFFERING FROM MYELOID NEOPLASIAS USING 5-AMINOIMIDAZOLE-4-CARBOXAMIDE

(75) Inventors: Thomas Cluzeau, Nice (FR); Patrick Auberger, Nice (FR); Guillaume Robert, Nice (FR)

(73) Assignees: Universite Nice Sophia Antipolis, Nice (FR); Centre Hospitalier Universitaire de Nice, Nice (FR); INSERM (Institut National de la Sante et de la Recherche Medicale), Paris (FR)

( * ) Notice: Subject to any disclaimer, the term of this patent is extended or adjusted under 35 U.S.C. 154(b) by 417 days.

(21) Appl. No.: 13/281,827

(22) Filed: Oct. 26, 2011

(65) Prior Publication Data

US 2013/0109648 A1 May 2, 2013

(51) Int. Cl.
*A61K 31/70* (2006.01)
*C07H 19/052* (2006.01)
*A61K 31/7056* (2006.01)

(52) U.S. Cl.
CPC .................................. *A61K 31/7056* (2013.01)
USPC ............................................ 514/43; 536/28.8

(58) Field of Classification Search
CPC .................................................. A61K 31/7056
See application file for complete search history.

(56) References Cited

U.S. PATENT DOCUMENTS

| 3,355,301 A | 11/1967 | Huang et al. |
| 4,912,092 A | 3/1990 | Gruber |
| 5,187,162 A | 2/1993 | Marangos et al. |
| 5,236,908 A | 8/1993 | Gruber et al. |
| 5,817,640 A | 10/1998 | Gruber et al. |
| 7,560,435 B2 | 7/2009 | Lopez Blanco et al. |

FOREIGN PATENT DOCUMENTS

| WO | 93/03734 A1 | 3/1993 |
| WO | 01/93873 A1 | 12/2001 |
| WO | 01/93874 A1 | 12/2001 |
| WO | 01/97816 A1 | 12/2001 |
| WO | 02/09726 A1 | 2/2002 |

OTHER PUBLICATIONS (R) Robert et al., "Acadesine Kills Chronic Myelogenous Leukemia (CML) Cells Through PKC-dependent Induction of Autophagic Cell Death," PLoS One, 4(11), e7889 (Nov. 18, 2009); only Abstract supplied.*
Cluzeau, Thomas et al., "Induction of autophagic cell death circumvents Azacitidine-resistance in myelodysplastic syndrom-derived cell lines", poster dated Dec. 4, 2010.
Cluzeau, Thomas et al., "Induction of autophagic cell death circumvents Azacitidine-resistance in myelodysplastic syndrom-derived cell lines", abstract dated Nov. 9, 2010.
Cluzeau, Thomas et al., "Azacitidine-resistant SKM1 myeloid cells are defective for AZA-induced mitochondrial apoptosis and autophagy", Cell Cycle, 10:14, pp. 1-5, Jul. 15, 2011.
Mangano, Dennis, "Effects of acadesine on Myocardial Infarction, Stroke, and Death Following Surgery: A Meta-analysis of the 5 International Randomized Trials", Jourmal of the American Medical Society, vol. 277(4), pp. 325-332, Jan. 22/29, 1997.

* cited by examiner

*Primary Examiner* — Lawrence E Crane
(74) *Attorney, Agent, or Firm* — Westerman, Hattori, Daniels & Adrian, LLP

(57) ABSTRACT

A method of treatment of a human patient suffering from myeloid neoplasias, includes administrating a therapeutically effective amount of 5-aminoimidazole-4-carboxamide (acadesine), acadesine precursors or acadesine derivatives.

7 Claims, 7 Drawing Sheets

METHOD FOR TREATING A HUMAN PATENT SUFFERING FROM MYELOID NEOPLASIAS USING 5-AMINOIMIDAZOLE-4-CARBOXAMIDE

The invention relates to the use of acadesine, acadesine precursors or acadesine derivatives, for the treatment of Myeloid Neoplasias in humans.

BACKGROUND OF THE INVENTION

Malignancies of the hematopoietic and lymphoid tissues include the lymphomas, leukemia, myeloproliferative neoplasms, plasma cell dyscrasias, histiocytic tumors, and dendritic cell neoplasms. Multiple classification schemes have been employed for these diseases over the years. The earliest classification system, namely the 2001 World Health Organization classification (WHO) classification, updated in 2008, is based on tissue architecture and the cytologic appearances of the neoplastic cells.

According to the WHO classification, there are two different types of Neoplasias arising from haematopoietic cells, namely:

1. Myeloid Neoplasias comprising Chronic Myeloproliferative Syndromes, Myelodysplasic Syndromes, an intermediate group called Chronic Myeloproliferative/Myelodysplasic syndromes and Acute Myeloid Leukaemia; and
2. Lymphoid Neoplasias comprising Hodgkin's and non-Hodgkin's Lymphomas, either B or NK/T, histiocytic and dendritic cell Neoplasias and finally Mastocytosis.

Considering this classification, it appears that the various Neoplasias arising from haematopoietic cells can be cured by different and specific treatments.

Thus, some Active Pharmaceutical Ingredients (for example Fludarabine, Melphalan, Bendamustine, Rituximab, Pralatrexate . . . ), that are recommended for the treatment of Lymphoid Neoplasias, are inefficient for treating Myeloid Neoplasias. It is therefore not possible to extrapolate the results obtained for the treatment of Lymphoid Neoplasias to the treatment of Myeloid Neoplasias.

Myeloid Neoplasias, as defined by the WHO (see above), are frequent diseases in elderly patients. Azacitidine (AZA) has been approved as an antitumor agent for the treatment of high-risk Myelodysplasic syndrome (MDS) or acute myeloid leukemia (AML) with multi-lineage dysplasia (blast count inferior at 30%) but a significant proportion of patients (approximately 40%) are refractory to this molecule. Abnormal methylation is supposed to support the effect of Azacitidine on leukemic cells but other mechanisms could also account for its additional antitumoral effect, including induction of apoptosis. The mechanisms of resistance to Azacitidine have been previously investigated in non-hematopoietic cancer cell lines.

Accordingly, a need exists for the treatment of patients which are resistant to Azacitidine treatment.

Acadesine 5'-monophospate, which is also named AICA ribotide and ZMP, has CAS RN 3031-94-5 and it is a natural occurring active metabolite of acadesine. Clinical studies in patients undergoing coronary artery bypass graft surgery demonstrate that treatment with acadesine before and during surgery can reduce early cardiac death and myocardial infarction (cf. D. T. Mangano, Journal American Medical Association 1997, vol. 277, pp. 325-332). Other patent documents relate to the use of acadesine for: preventing tissue damage due to decreased blood flow (U.S. Pat. Nos. 4,912,092, 5,817, 640); treating neurodegenerative conditions (U.S. Pat. No. 5,187,162); preventing injury to the central nervous system (U.S. Pat. No. 5,236,908); treating obesity (WO 0193873); treating type diabetes (WO 0197816) and treating conditions associated with insulin resistance (WO 0209726). There are patent documents which relate to the use of acadesine 5'-monophosphate as flavouring material (U.S. Pat. No. 3,355,301), anticholestermic/anti-hyperlipemic agent (WO 9303734), antiobesity agent (WO 0193874) and antidiabetic agent (WO 0197816).

More recently, a patent has been granted for a method for treating a human patient suffering from a B-cell lymphoproliferative disorder, comprising the administration of a therapeutically effective amount of acadesine or an acadesine precursor (U.S. Pat. No. 7,560,435).

However, nothing is mentioned or suggested in the prior art in relation to the use of acadesine, acadesine 5'-monophosphate or any of their prodrugs for treating specifically Myeloid Neoplasias such as Chronic Myeloproliferative Syndromes, Myelodysplasic Syndromes, an intermediate group called Chronic Myeloproliferative/Myelodysplasic syndromes and Acute Myeloid Leukaemia.

SUMMARY OF THE INVENTION

As a need exists for treating patients which are resistant to Azacitidine (AZA) treatment, the inventors generated AZA-resistant SKM1 myeloid cells (called hereafter AZA-R) in order to investigate the mechanisms associated with Azacitidine resistance in vitro.

The inventors have shown that AZA-R cells exhibit impaired mitochondrial membrane permeabilization and caspase activation in response to Azacitidine compared to their Azacitidine sensitive (AZA-S) counterpart. Azacitidine induces also LC3-II accumulation and Cathepsin B activity in AZA-S and AZA-R cells, two hallmarks of autophagy. Considering the above, the inventors concluded that autophagy is functional in AZA-S (sensitive) and AZA-R (resistant) cells and could be a mechanism to induce, if there is an impaired apoptosis.

Therefore, the inventors used Acadesine in order to induce autophagic cell death in cell lines and in medullar cells of Myelodysplasic syndrome and acute myeloid leukemia patients treated with Azacitidine. Surprisingly, this molecule induced decrease of cell metabolism in these cells. This allows considering Acadesine as a new treatment for Myelodysplasic and/or acute myeloid leukemia patients. The inventors have shown that acadesine exerted an anti-leukemic effect through induction of autophagic cell death in CML cell lines.

It has therefore been found that an Acadesine treatment is efficient for the treatment of Myeloid Neoplasias comprising Chronic Myeloproliferative Syndromes, Myelodysplasic Syndromes, an intermediate group called Chronic Myeloproliferative/Myelodysplasic syndromes and Acute Myeloid Leukaemia.

In accordance with a first aspect, the invention concerns a method for treating a human patient suffering from Myeloid Neoplasias, comprising administrating a therapeutically effective amount of a compound of formula (I):

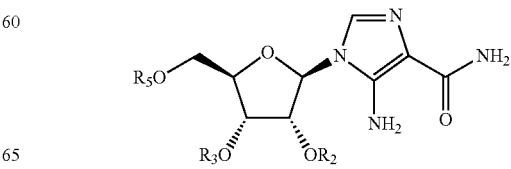

or a pharmaceutically acceptable solvate or salt thereof, together with appropriate amounts of pharmaceutically acceptable diluents or carriers; wherein, —R2, —R3 and —R5 are radicals independently selected from the group consisting of —H, —PO(OH)$_2$, —PO(OH)—O—PO(OH)$_2$ and —PO(OH)—O—PO(OH)—O—PO(OH)$_2$, —CO—R' and —CO—OR'; R' being a hydrocarbyl radical up to twelve carbon atoms, which may be aliphatic-including alkyl, alkenyl, and alkynyl groups and groups which have a mixture of saturated and unsaturated bonds, alicyclic, aryl or a combination thereof; wherein R' may be a radical from a straight-chain, a branched-chain, a cycle or a combination thereof; R' may have one or more hydrogen atoms substituted by one or more halogen atoms, and/or by one or more $(C_1$-$C_4)$-alkyl groups; R' may have one or more CH$_2$ groups substituted by one or more NH, O and/or S groups; and R' may have one or more CH groups substituted by one or more N atoms.

Preferably, in the compound of formula (I), —R2, —R3 and —R5 are radicals independently selected from the group consisting of —H, —PO(OH)$_2$, —PO(OH)—O—PO(OH)$_2$ and —PO(OH)—O—PO(OH)—O—PO(OH)$_2$.

More preferably, the compound of formula (I) is selected from the group consisting of acadesine and acadesine 5'-monophosphate.

The method according to the invention is intended for the treatment of Myeloid Neoplasias disorder, chosen among Chronic Myeloproliferative Syndromes, Myelodysplasic Syndromes, an intermediate group called Chronic Myeloproliferative/Myelodysplasic syndromes and Acute Myeloid Leukaemia.

According to a preferred embodiment of the invention, the method according to the invention is intended for the treatment of Myelodysplasic syndrome.

According to another preferred embodiment of the invention, the method according to the invention is intended for the treatment of Acute myeloid leukemia.

Other features and aspects of the present invention will be apparent from the following description and the accompanying drawings.

BRIEF DESCRIPTION OF THE DRAWINGS

In FIG. 6, AZA-S SKM1 cells were incubated for 24 h with increased doses of ACA (acadesine). In FIG. 7, AZA-R SKM1 cells were incubated for 24 h with increased doses of ACA. Cell metabolism was then assessed by using the XTT assay in both assays. Results represent the mean+/−SEM of three independent experiments made in quadruplicates.

FIG. 10 shows that, conversely to Azacitidine, acadesine inhibits cell metabolism in AZA-S cells independently of caspase activation. For this experiment, AZA-S SKM1 cells were incubated for 24 h with 1 µM Azacitidine or 1 mM Acadesine in either the presence or the absence of 50 µM Z-VAD-fmk. Cell metabolism was assessed using the XTT assay. Results represent the mean+/−SEM of three independent experiments achieved in quadruplicates. FIG. 11 show that acadesine inhibits cell metabolism in AZA-R cells. For this experiment, AZA-R SKM1 cells were incubated for 24 h with 1 µM Azacitidine or 1 mM Acadesine in either the presence or the absence of 50 µM Z-VAD-fmk. Cell metabolism was assessed using the XTT assay. Results represent the mean+/−SEM of three independent experiments achieved in quadruplicates.

DETAILED DESCRIPTION OF THE INVENTION

In the following examples, bone marrow samples were collected from 15 patients treated by Azacitidine. All patients had a diagnosis of MDS or AML with less of 30% of blasts and IPSS scoring intermediate-2 or higher. The diagnosis of MDS or AML was based on standard WHO criteria (Vardiman et al., Blood 2009). Patients were to receive Azacitidine at the FDA/EMEA approved schedule (75 mg/m$^2$/d, 7 d/4 weeks). Patients having received one or more than one cycle of Azacitidine and who had bone marrow evaluation after at least four cycles, or who died or progressed before completion of four cycles were considered evaluable (the last two groups were considered as treatment failures). Responses were scored according to IWG 2006 criteria for MDS and to Cheson et al. (JCO 2003) for AML.

EXAMPLE 1

Apoptosis in AZA-R SKM1 Cells

In this experiment, Azacitidine resistant SKM1 (AZA-R SKM1) cells have been used in order to compare the induction of apoptosis by Azacitidine in AZA-R SKM1 or Azacitidine sensitive SKM1 (AZA-S SKM1) cells.

To obtain AZA-R SKM1 cells, human SKM1 cells were purchased from the DSMZ (Braunschweig, Germany) and grown at 37° C. under 5% CO2 in RPMI 1640 Medium (Gibco BRL, Paisley, UK) supplemented with 5% fetal calf serum, 50 units/ml penicillin, 50 µg/ml streptomycin and 1 mM sodium pyruvate. From the SKM-1 myeloid cell line (8), called hereafter AZA-S SKM1 cells, AZA-R SKM1 cells were established by iterative addition into the culture medium of increasing concentrations of AZA. Briefly, cells were exposed to Azacitidine starting from 100 nmol/L and Azacitidine concentration was doubled every week. After 6 months, cells that continued to grow in the presence of 25 µmol/L Azacitidine were obtained. The parental cell line was maintained in parallel cultures without Azacitidine and is used hereafter as AZA-sensitive SKM1 cells (AZA-S SKM1). As resistance was partly reversible when Azacitidine was withdrawn from the culture medium, AZA-R cells were maintained continuously in the presence of 1 µM AZA.

Figure 1:
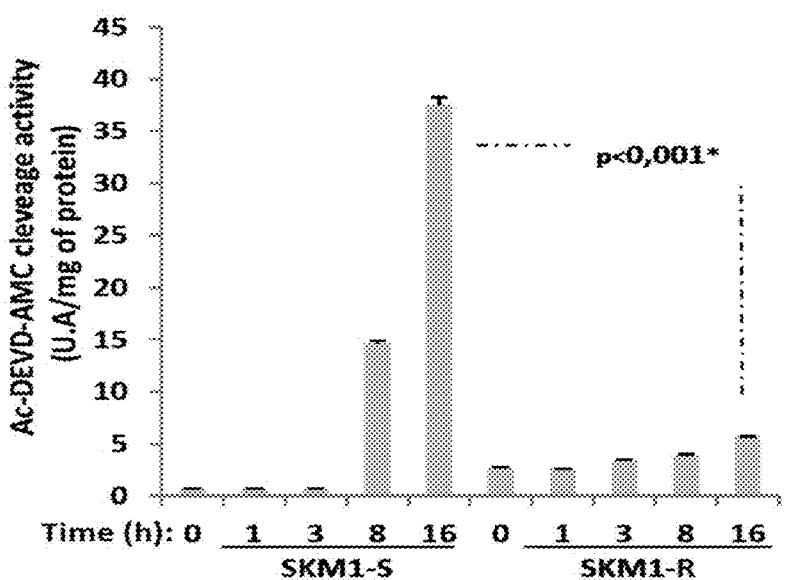
FIG. 1 illustrates AZA-induced apoptosis in AZA-SKM1 cells as assessed by caspase 3 assay. In this figure, cells were incubated for different times with 1 µM Azacitidine. Caspase activities were determined in quadruplicates using 0.2 mM Ac-DEVD-AMC as substrate.
Figure 2:
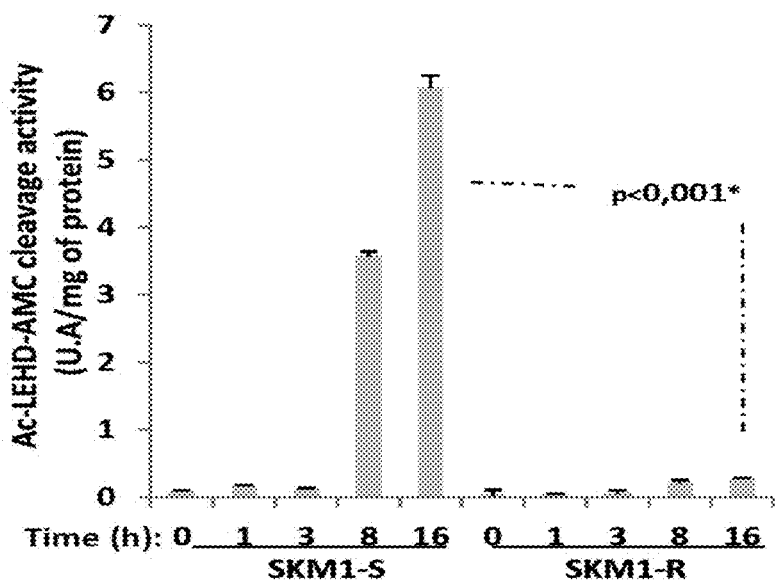
FIG. 2 illustrates AZA-induced apoptosis in AZA-SKM1 cells as assessed by caspase 9 assay. In this figure, cells were incubated for different times with 1 µM Azacitidine. Caspase activities were determined in quadruplicates using 0.2 mM Ac-LEHD-AMC as substrate.
Figure 3:
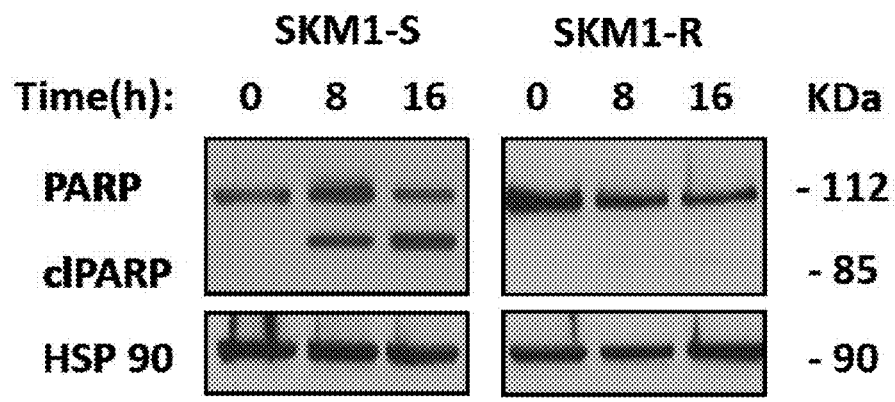
FIG. 3 shows the absence of cleavage of PARP in AZA-R cells. In this experiment, PARP cleavage was assessed by western-blot on cell extracts prepared from AZA-S and AZA-R cells incubated for 16 h with 1 µM Azacitidine.

In this experiment, as shown in FIGS. 1 and 2, treatment of the SKM1 myeloid cell line (AZA-S SKM1) with 1 µM Azacitidine for 8-16 h induced caspase 3 (FIG. 1) and caspase 9 (FIG. 2) activation as assessed by the hydrolysis of Ac-DEVD-AMC and LEHD-AMC respectively. By contrast no caspase activities was induced in AZA-R SKM1 cells treated with AZA, indicating that AZA-R SKM1 cells are resistant to AZA-mediated apoptosis. This was further confirmed by analyzing the cleavage of the caspase 3 substrate Poly-ADP-Ribose Polymerase (PARP) by Western Blot since no AZA-mediated cleavage of PARP was detected in AZA-R SKM1 cells (FIG. 3).

For these caspase assays, $10^6$ cells/mL were incubated for different times at 37° C. with 1 µM Azacitidine. After stimulation, cells were lysed for 30 min at 4° C. Cellular extracts were incubated in 96-well plates with either Ac-DEVD-AMC (caspase 3) or Ac-LEHD-AMC (caspase 9) as substrates. Each experiment was performed in quadruplicates and repeated at least three times.

For the Western Blot analysis, cells were first stimulated by 1 µM Azacitidine for the indicated times, then cells were harvested and lysed in buffer containing 1% Triton X-100 and supplemented with protease and phosphatase inhibitors (Roche Diagnostics) as previously described. Lysates were pelleted, and 50 µg of protein were analyzed by SDS-PAGE.

EXAMPLE 2

Alteration of Basal and Azacitidine Mediated Autophagy in AZA-R SKM1 Cells

Figure 4:
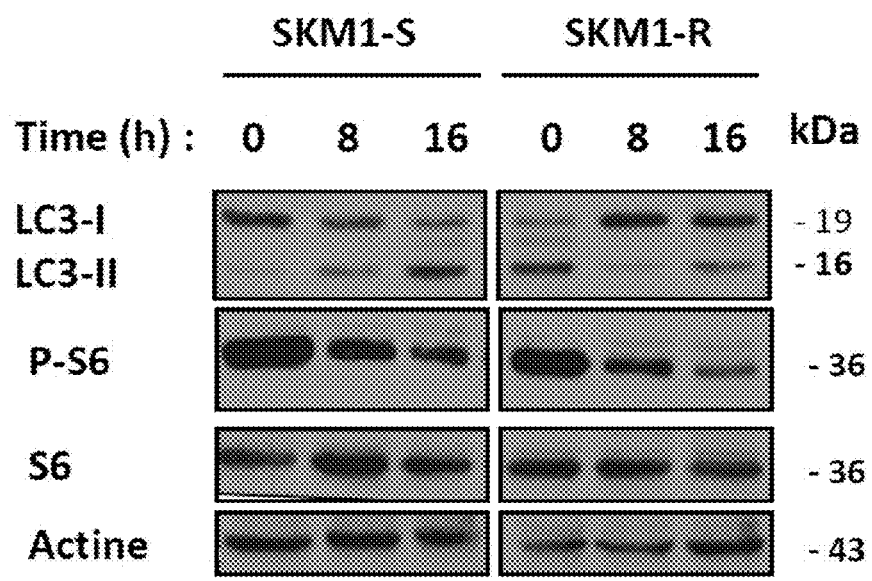
FIG. 4 illustrates increased basal autophagy and decreased AZA-mediated autophagy in AZA-R cells. In this experiment, cells were incubated for increasing times with 1 µM AZA. LC3-I and LC3-II, S6 ribosomal protein (P-S6), and its phosphorylated form were visualized by western blot.
Figure 5:
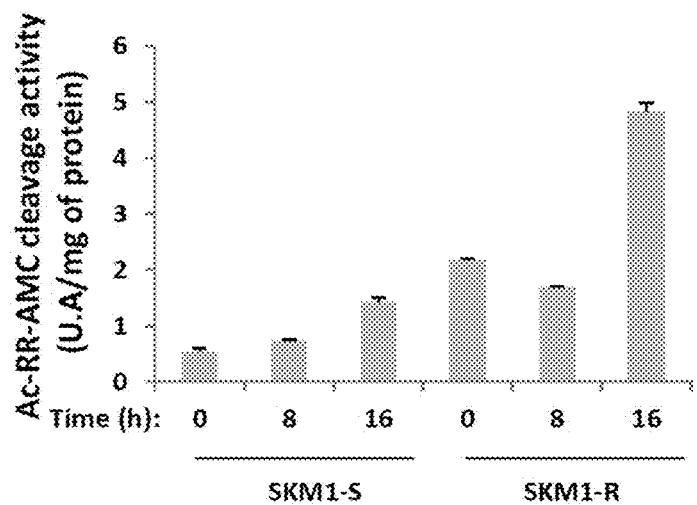
FIG. 5 shows Cathepsin B activity is increased in AZA-R cells treated with AZA. For this experiment cells were incubated for increasing times with 1 µM AZA. Cell extracts were prepared and Cathepsin B activity determined in quadruplicatesusing Z-RR-AMC as substrates.

The inventors investigated whether Azacitidine may affect autophagy in AZA-S SKM1 and AZA-R SKM1 cells. Azacitidine triggered a time-dependent accumulation of LC3-II, a hallmark of autophagy, in AZA-S cells (FIG. 4). Importantly, basal autophagy was significantly higher in AZA-R cells compared to their Azacitidine sensitive counterpart but was not further stimulated by AZA. Autophagy induction was accompanied by an inhibition of ribosomal protein S6 phosphorylation, an index of mTOR inhibition in both cell lines. In addition, higher basal level of Cathepsin B activity was detected in AZA-R compared to AZA-S cells confirming that AZA-R cells exhibited increased autophagy (FIG. 5).

For these Cathepsin B assays, $10^6$ cells/mL were incubated for different times at 37° C. with 1 µM Azacitine. After stimulation, cells were lysed for 30 min at 4° C. Cellular extracts were incubated in 96-well plates with Ac-RR-AMC (Cathepsin B) as substrate. This experiment was performed in quadruplicates and repeated at least three times.

EXAMPLE 3

Figure 6:
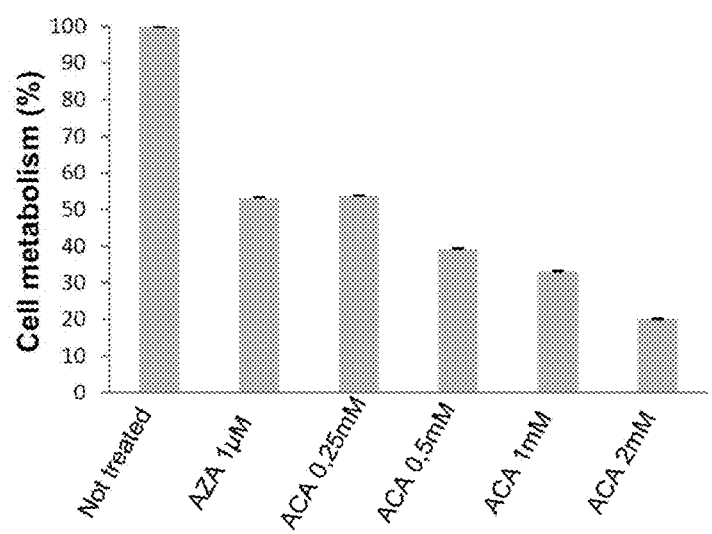
FIGS. 6 and 7 illustrate respectively the efficiency of acadesine in SKM1-S and SKM1-R cells.
Figure 7:
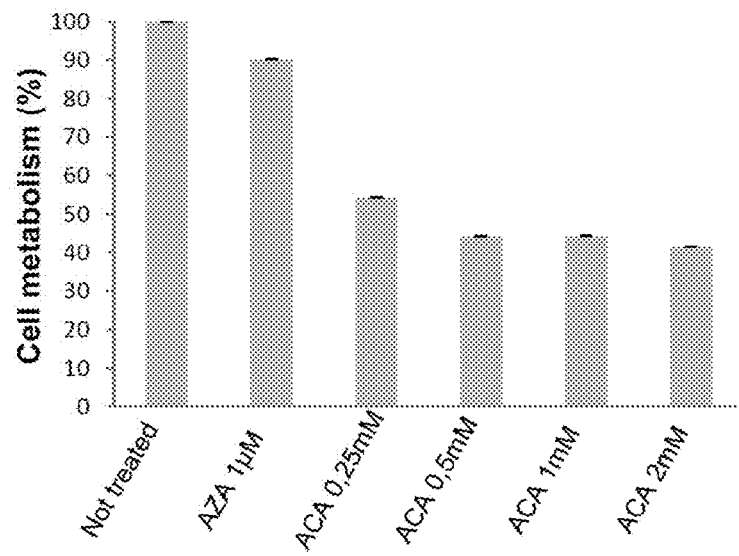

Acadesine Induces a Dose-Dependent Inhibition of Cell Metabolism in AZA-S and AZA-R Cells Incubation of AZA-S SKM1 and AZA-R SKM1 cells with different doses of Acadesine (ACA) led to a dose-dependent inhibition of cell metabolism. In both cases, half-maximal inhibition was obtained for 0.25 mM Acadesine (FIGS. 6 and 7). For the rest of the experiments, the maximal dose of 1 mM was chosen.

For the cell metabolism assessment, $15 \times 10^3$ cells were incubated in a 96-well plate for different times with various concentrations of Azacitidine in a final volume of 100 µL. After 16, 24 or 48 h, 50 µL of XTT reagent was added to each well. The absorbance of the formazan product, reflecting cell metabolism, was measured at 490 nM. Each assay was performed in quadruplicate.

EXAMPLE 4

Acadesine Induces Autophagic Cell Death in AZA-R SKM1 Cell Line

Figure 8:
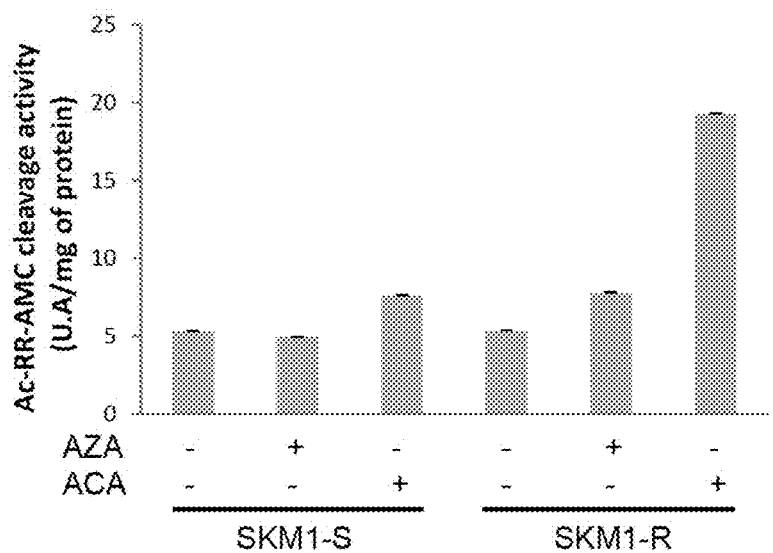
FIG. 8 illustrates that Acadesine stimulates Cathepsin B activity in AZA-R cells. In this experiment cells were incubated for 24 h with 1 µM Azacitidine or 1 mM ACA. Cell extracts were prepared and Cathepsin B activity was determined in quadruplicates using Z-RR-AMC as substrate.
Figure 9:
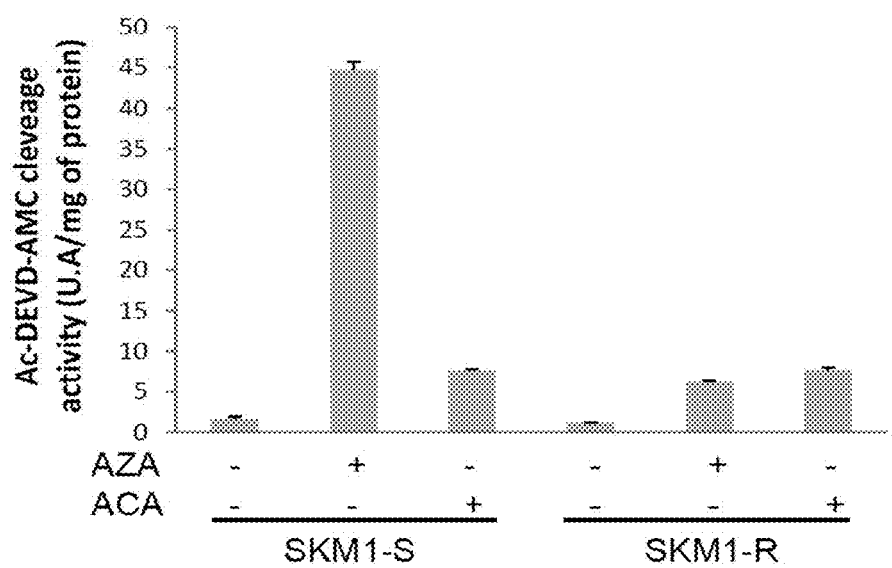
FIG. 9 show that Acadesine does not induce apoptosis in AZA-S and AZA-R cells. In this experiment, cells were incubated for 24 h with 1 µM Azacitidine or 1 mM ACA. Cell extracts were then prepared and caspase activities were determined in quadruplicates using 0.2 mM Ac-DEVD-AMC as substrate.

The inventors observed an increase of Cathepsin B activity in ACA-treated AZA-R SKM1 cells but not in AZA-S SKM1 cells (FIG. 8). The inventors also confirmed that Azacitidine induced caspase 3 activity in AZA-S SKM1 cells whereas there was no increase in AZA-R SKM1 cells (FIG. 9). Selectively, these findings established that Acadesine is mainly active in AZA-R SKM1 cells and that its effect was mediated through induction of autophagy.

EXAMPLE 5

Acadesine Inhibits Cell Metabolism in AZA-S SKM1 and AZA-R SKM1 Cells as Well

Figure 10:
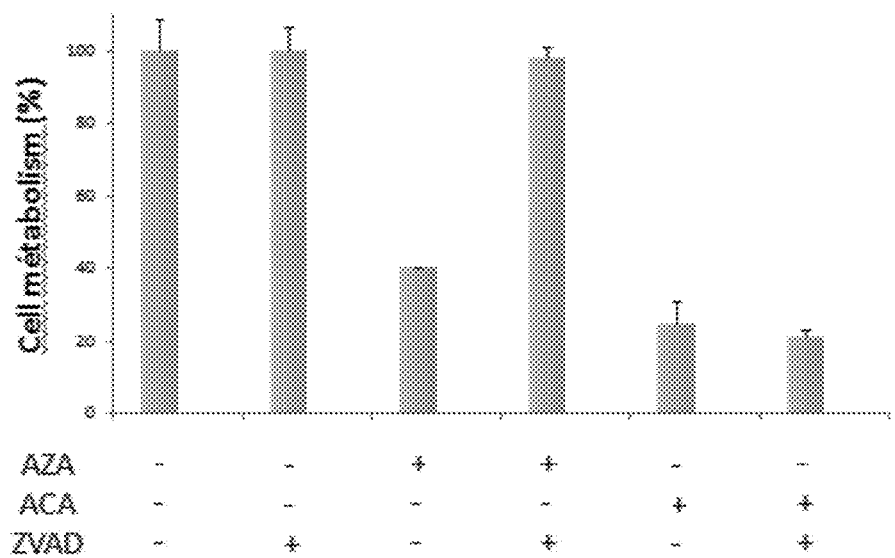
FIGS. 10 and 11 illustrate the efficacy of acadesine in AZA-S and AZA-R cells.
Figure 11:
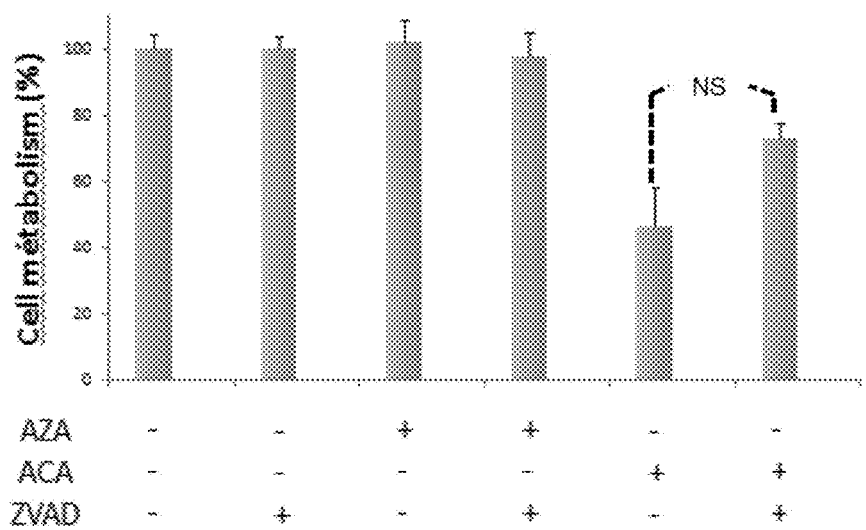

As expected 1 µM Azacitidine efficiently reduced cell metabolism in SKM1-S cells (FIG. 10) but not in its resistant counterpart (AZA-R SKM1) (FIG. 11). This inhibitory effect of Azacitidine in AZA-S SKM1 was reverted by Z-VAD-fmk, a pan caspase inhibitor involving caspases in this process. Acadesine drastically inhibited cell metabolism in identical conditions but independently of caspases (FIG. 10).

Therefore, Acadesine can induce loss of cell metabolism in a caspase deficient context. Accordingly, the inventors investigated the effect of Acadesine reduced cell viability by 60% in AZA-R SKM1 cells (FIG. 11).

The cell metabolism assessment was made in an identical manner as described in example 3.

EXAMPLE 6

Acadesine is Highly Efficient to Kill Primary Cells from AZA-R MDS Patients

Figure 12:
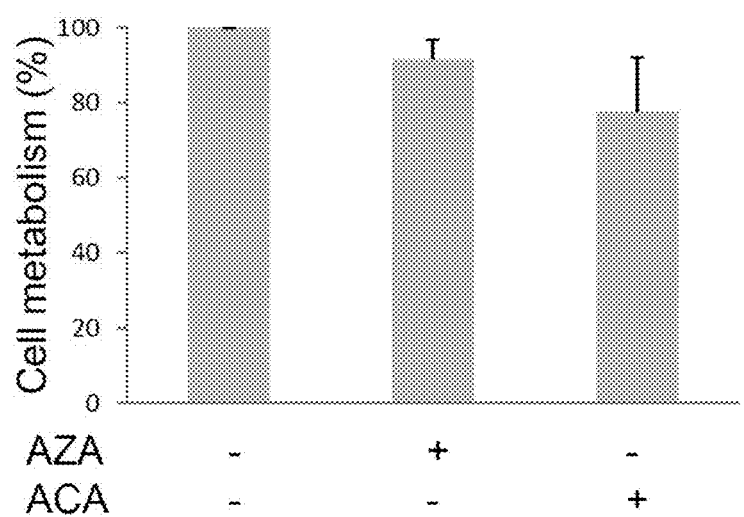
FIG. 12 illustrates that acadesine inhibits cell metabolism in AZA-S patients (n=7). For this experiment, bone marrow cells of 7 AZA-sensitive patients were treated with 1 µM Azacitidine or 1 mM Acadesine. Cell metabolism was assessed using the XTT assay. Results represent the mean+/−SEM of three independent experiments achieved in quadruplicates.
Figure 13:
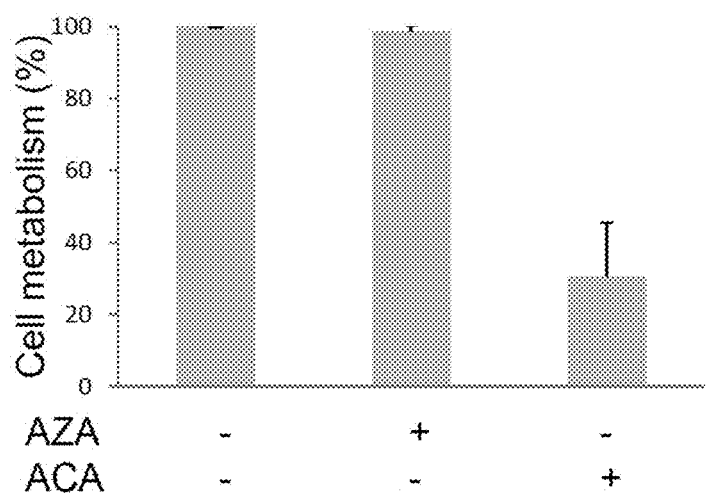
FIG. 13 show that acadesine strongly inhibits cell metabolism in AZA-R patients, more than AZA-S cells. For this experiment, bone marrow cells of 8 AZA-resistant patients were treated with 1 µM Azacitidine or 1 mM Acadesine. Cell metabolism was assessed using the XTT assay. Results represent the mean+/−SEM of three independent experiments achieved in quadruplicates.
Figure 14:
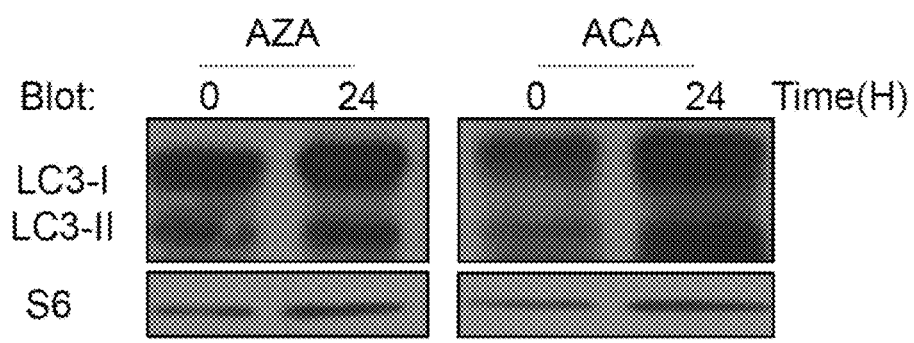
FIG. 14 shows the induction of autophagy by Acadesine in MDS patients. In this experiment LC3 I and LC3 II expression was assessed by Western-Blot on cell extracts prepared from AZA-resistant patient bone marrow cells incubated for 24 h with 1 mM Acadesine.

Acadesine efficiency was next investigated on fifteen primary cell samples from MDS or AML patients treated or not by AZA. Samples from seven Azacitidine sensitive patients (FIG. 12) and eight samples from Azacitidine resistant patients were included in this experiment and analyzed by the XTT assay (FIG. 13). As previously described for AZA-R SKM1 cells, Acadesine was more efficient to kill cells from Azacitidine resistant patients. Finally, induction of autophagy by Acadesine was confirmed in one Azacitidine resistant patient, by assessment of the conversion of LC3-I into LC3-II using western blotting (FIG. 14).

The invention claimed is:

1. A method for treating a human patient suffering from myeloid neoplasias, comprising administrating a therapeutically effective amount of a compound of formula (I):

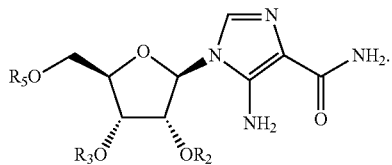

salt thereof, together with appropriate amounts of pharmaceutically acceptable diluents or carriers; wherein, $R_2$, $R_3$ and $R_5$ are radicals independently selected from the group consisting of —H, —PO(OH)$_2$, —PO(OH)—O—PO(OH)$_2$, —PO(OH)—O—PO(OH)—O—PO(OH)$_2$, —CO—R' and —CO—OR'; R' being a hydrocarbyl radical up to twelve carbon atoms, which may be an aliphatic substituent selected from alkyl, alkenyl, and alkynyl groups and groups which have a mixture of saturated and unsaturated bonds, alicyclic, aryl, and a combination thereof; wherein R' may be a radical selected from a straight-chain, a branched-chain, a cyclic moiety, and a combination thereof; R' may have one or more hydrogen atoms substituted for by one or more halogen atoms, and/or by one or more ($C_1$-$C_4$)-alkyl groups; R' may have one or more $CH_2$ groups substituted for by one or more NH, O and/or S groups; and R' may have one or more CH groups substituted by one or more N atoms.

2. The method according to claim 1, wherein in the compound of formula (I), —$R_2$, —$R_3$ and —$R_5$ are radicals independently selected from the group consisting of —H, —PO(OH)$_2$, —PO(OH)—O—PO(OH)$_2$ and —PO(OH)—O—PO(OH)—O—PO(OH)$_2$.

3. The method according to claim 2, wherein the compound of formula (I) is selected from the group consisting of acadesine and acadesine 5'-monophosphate.

4. The method according to claim 3, wherein the compound of formula (I) is acadesine.

5. The method according to claim 1, wherein the myeloid neoplasias disorder is selected from chronic myeloproliferative syndromes, myelodysplasis syndromes, an intermediate group called chronic myeloproliferative/myelodysplasisc syndromes, and acute myeloid leukaemia.

6. The method according to claim 5, wherein the myeloid neoplasias disorder is the myelodysplasis syndrome.

7. The method according to claim 5, wherein the myeloid neoplasias disorder is acute myeloid leukaemia.

* * * * *